United States Patent [19]

Miyata et al.

[11] Patent Number: 5,099,839
[45] Date of Patent: Mar. 31, 1992

[54] CATHETER FOR TEMPORARY PACING

[75] Inventors: Shinichi Miyata, Yokohama; Takashi Kawabata, Hasuda; Kiyoshi Takagi, Yokohama; Masaru Miyahara, Tokyo; Takashi Tsuji, Fujisawa; Shigeto Yoshida; Masayuki Horikawa, both of Yokohama; Fumiharu Iwai, Kodaira, all of Japan

[73] Assignee: Nippon Zeon Co., Ltd., Tokyo, Japan

[21] Appl. No.: 445,673

[22] PCT Filed: Mar. 29, 1989

[86] PCT No.: PCT/JP89/00328
§ 371 Date: Nov. 27, 1989
§ 102(e) Date: Nov. 27, 1989

[87] PCT Pub. No.: WO89/09081
PCT Pub. Date: Oct. 5, 1989

[30] Foreign Application Priority Data

Mar. 29, 1988 [JP] Japan .................. 63-73219

[51] Int. Cl.⁵ .................................. A61N 1/05
[52] U.S. Cl. ...................... 128/419 P; 128/419 PG
[58] Field of Search ............ 128/419 P, 419 PG, 786; 206/571

[56] References Cited

U.S. PATENT DOCUMENTS

4,160,505 7/1979 Rauschenberger ............... 206/571
4,602,645 7/1986 Barrington et al. ............... 128/786
4,708,144 11/1987 Hamilton et al. ............ 128/419 PG Primary Examiner—William E. Kamm
Assistant Examiner—Scott M. Getzow
Attorney, Agent, or Firm—Armstrong, Nikaido, Marmelstein, Kubovcik & Murray

[57] ABSTRACT

A temporary pacing catheter having an integrally attached temporary pacemaker function is disclosed. The pacemaker integrally built in this catheter for temporary pacing has a very small size and can be fixed to the body of a patient, and therefore, the patient can be transferred conveniently. Furthermore, if this catheter is packaged in the sterilized conditions, problems or another's help required for the connection of the catheter to the pacemaker and the like operations in the conventional technique can be avoided, and therefore, the packaged catheter is suitably used for an emergency treatment. Moreover, if a balloon is attached and arranged so that when the balloon is inflated, the balloon envelopes an electrode at the distal end, the catheter can be caused to flow in the heart and blood vessel safely and promptly.

3 Claims, 5 Drawing Sheets

CATHETER FOR TEMPORARY PACING

TECHNICAL FIELD

The present invention relates to a catheter for temporary pacing, which is mainly used for an emergency treatment.

BACKGROUND ART

Temporary pacing is used as an emergency treatment for atrioventricular block of the heart or right bundle branch block caused by serious arrhythmia, myocardial infraction or the like. By the term "temporary pacing" used herein is meant pacing not using a pacemaker implanted in a body. Namely, in temporary pacing, only a pacing electrode is inserted into a body, and the proximal end of an electrode catheter is located outside the body of a patient. Connection between wire connected to the electrode and a pacemaker is performed outside the body of the patient and the pacemaker is generally set outside the body.

In contrast, in implanted pacing, a connecting portion between an implantable type pacemaker and an implantable type pacemaker lead is embedded in the body, and further, the pacemaker is generally implanted in the body of a patient.

When the catheter for temporary pacing is applied, for example, a peripheral vein such as the femoral vein or subclavian vein is punctured by a catheter introducer through an incised portion of the skin. The catheter for temporary pacing is inserted through this introducer and the distal end of the catheter is held on the apex of the right ventricle, and positive and negative leads at the proximal end of the catheter are connected to terminals of the temporary pacemaker and a switch is turned on to start the pacemaker and initiate pacing. The stimulation rate, the stimulation output amplitude and the electrocardiographic sensitivity are adjusted to desired levels and the catheter-inserted portion of the skin is sutured.

Current temporary pacemakers are generally of the "demand" type, and in a pacemaker of this type, for example, the stimulation rate can be analogically adjusted to a desired level (for example, 30 to 150 pulses per minute) and similarly, the stimulation output amplitude can be analogically adjusted to a desired level (for example, 0.1 to 15 V). Moreover, the pacemaker has a mechanism for manually adjusting the electrocardiographic sensitivity to a desired level (for example, 0.5 to 20 mV). At least three variable resistors should be built into the pacemaker for performing these analogical adjustments. The abovementioned three adjustment mechanisms should be disposed, although temporary pacemakers comprising still another mechanism capable of the analogical adjustment have been proposed. Each of these variable resistors should be strong and durable enough that it can be used repeatedly, and the mechanical shaft of the variable resistor should have a waterproof and sterilizable structure. These variable resistors generally have a round shape having a diameter of about 19 mm and a thickness of about 20 mm. Accordingly, the pacemakers come in a large size such that the length is about 15 cm, the width is 10 cm, and the height is about 3 cm and it is difficult to fix them to the body surface of a patient. Therefore, the pacemakers must be arranged apart from the body surface portion, and thus handling is difficult and complicated. Moreover, at the transfer of a patient, often the catheter is pulled by the temporary pacemaker and the catheter is pulled out.

Another important problem resides in the connection of the catheter for temporary pacing to the temporary pacemaker. To prevent infection, the hands and fingers of an operator inserting the catheter must be carefully disinfected prior to the operation of the catheter. To confirm that pacing will be carried out smoothly, the catheter is connected to the temporary pacemaker after the insertion of the catheter, and a test working is conducted. Since the temporary pacemaker has a structure in which sterilization is impossible or the temporary pacemaker is so large and heavy that it cannot be sterilized, the temporary pacemaker is used in the non-sterilized condition. Moreover, when pacing is not smoothly carried out, often the operator handles the catheter again, but the operator is not allowed to touch the unclean temporary pacemaker. In general, another operator adjusts at least three variable resistors as mentioned above according to the condition of a patient. But, in an emergency, for example, during the night, it is often difficult to obtain two operators, and this situation is a serious problem for a life-saving emergency treatment fighting the clock.

For insertion and indwelling to the intended part, a heavy metal compound or a radiopaque medium are incorporated into the body tube of the catheter for temporary pacing and the operation is carried out under fluoroscopic observation. Alternatively, a pressure-measuring apparatus is connected to the lumen of the catheter, communicating with the distal end opening, on the side of the proximal end of the catheter, and the catheter is inserted and held while measuring the pressure at the distal end of the catheter. Furthermore, there is already known a catheter for temporary pacing, which is constructed by attaching a balloon to the top end of a catheter as mentioned above so that the catheter can float and flow in the heart and blood vessels.

In the above-mentioned conventional catheter for temporary pacing, the distal end electrode is formed from a hard metal such as stainless steel or platinum, and even in the balloon catheter for temporary pacing, the distal end electrode projects over the balloon when the balloon is inflated. Accordingly, where the conventional pacing catheter is inserted into the intended part through the skin and held on this part, the heart and blood vessels are often damaged by the distal end electrode, and if the catheter is forcibly proceeded, there is a risk of perforation.

The inventors carried out investigations into ways of solving the foregoing problems, and noted that if the size of the temporary pacemaker function is diminished and this function is embedded in the pacing catheter, the pacemaker function can be used in the state attached to the body of a patient and handling inconvenience is eliminated. It also was noted that, if a catheter having a temporary pacing function therein is packaged in the sterilized condition, a second operator required for connecting the temporary pacemaker to the pacing catheter becomes unnecessary. The inventors further investigated the possibility of integration and sterilization.

Moreover, the inventors investigated ways in which a catheter for temporary pacing comprising a balloon attached to the vicinity of the distal end is developed, in which the distal end electrode is not projected over the balloon when the balloon is inflated, and as a result, the present invention was completed.

DISCLOSURE OF THE INVENTION

In accordance with one aspect of the present invention, there is provided a catheter for temporary pacing, which comprises an integrally attached temporary pacemaker function.

A temporary pacemaker of this catheter for temporary pacing, which generally has a pacing function in which one or both of the stimulation rate and the stimulation output amplitude are fixed, and which preferably has a pacing function in which one or both of the stimulation rate and the stimulation output amplitude are fixed and a mechanism for automatically adjusting the electrocardiographic input sensitivity is disposed.

In accordance with another aspect of the present invention, there is a packaged catheter for temporary pacing, which comprises a catheter for temporary pacing, sterilized and packaged with a packaging material.

In accordance with still another aspect of the present invention, there is a pacing catheter having an electrode arranged at the distal end and a balloon attached to the vicinity of the distal end of the catheter and arranged to envelop the electrode at the distal end when the balloon is inflated.

BRIEF DESCRIPTION OF THE DRAWINGS

FIGS. 4A and 4B show waveforms indicating the changes with the lapse of time of the endocardial potential, obtained in the circuit shown in FIG. 3, wherein FIG. 4A shows the results obtained when the electrocardio-input is large and FIG. 4B shows the results obtained when the electrocardio-input is small;

BEST MODE FOR CARRYING OUT THE INVENTION

In the catheter for temporary pacing according to the present invention, which comprises an integrally attached temporary pacemaker function, the size of the temporary pacemaker should be small. To make a pacemaker having a small size, the inventors selected the minimum and necessary functions for the temporary pacemaker for emergency case, fixed the stimulation rate and stimulation output amplitude as suitable fixed values, and adopted the automatic adjustment of the electrocardio-sensitivity. More specifically, in the case of an emergency life-saving measures to be conducted in a short time, no problem arises even if the stimulation rate is fixed to a specific value in the range of from 60 to 120 pulses per minute, for example, 100 pulses per minutes, and the stimulation output amplitude is fixed to a specific pulse output having a pulse width of from 1 to 5 m-sec and a pulse amplitude of 1 to 5 V, for example, a pulse width of 3 m-sec and a pulse peak height of 2.5 V, and therefore, by arranging a function of fixing the pulse width and pulse amplitude as mentioned above and automatically adjusting the electrocardio-sensitivity, the size of the temporary pacemaker can be diminished to an extent such that the length is about 7 cm, the width is about 3 cm, and the height is about 1 cm.

The catheter for temporary pacing according to the present invention will now be described in detail with reference to the accompanying drawings.

Figures 1, 2:
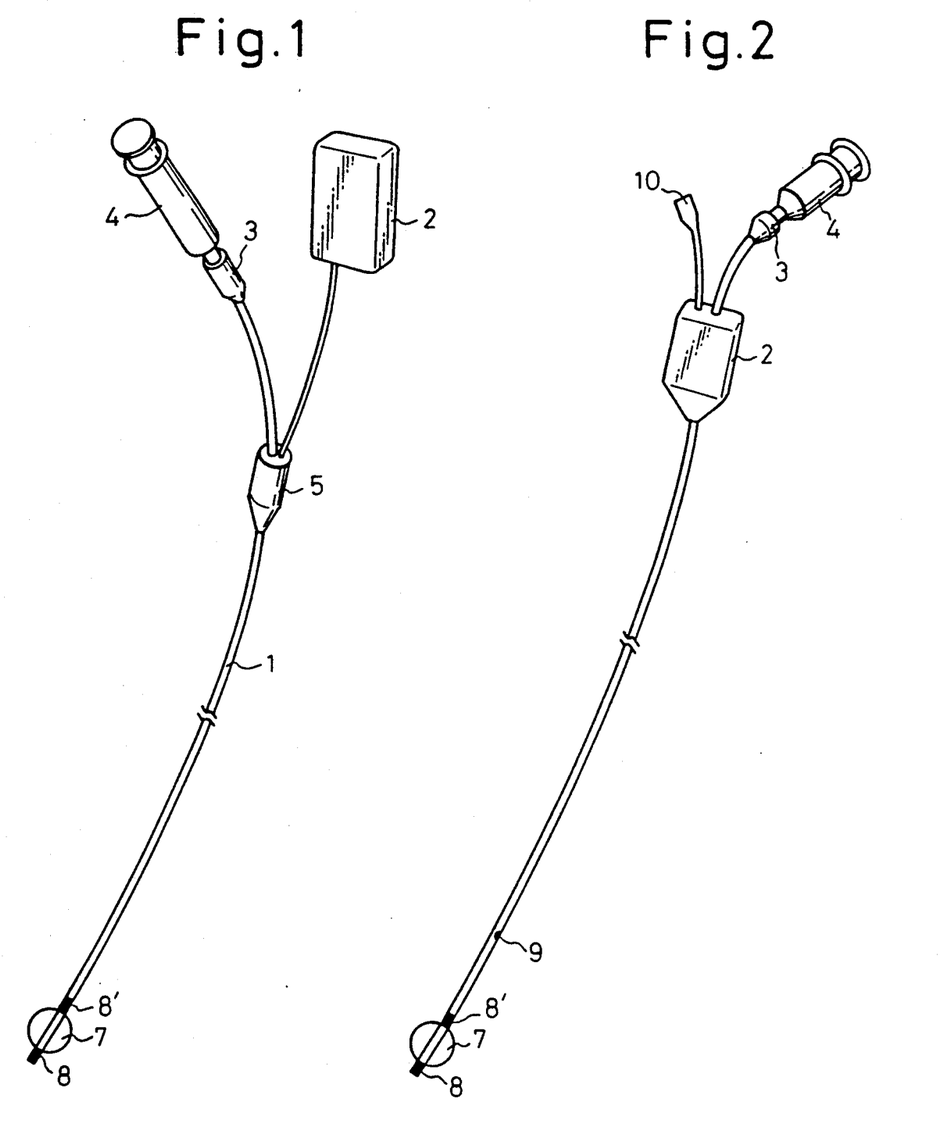
FIG. 1 is a perspective view illustrating an embodiment of the catheter for temporary pacing according to the present invention.
FIG. 2 is a perspective view illustrating another embodiment of the catheter for temporary pacing according to the present invention.

In the catheter for temporary pacing shown in FIG. 1, pacing electrodes 8 and 8, and a balloon 7 are attached to the distal end of the catheter, and a syringe 4 is arranged at the proximal end 3 of the catheter. The syringe 4 is connected to the balloon 7 at the distal end of the catheter through a catheter tube 1, and the balloon 7 can be inflated or deflated by operating the syringe 4. A temporary pacemaker function portion 2 is attached to a branched portion 5 of the catheter, and this temporary pacemaker function portion 2 is connected to the pacing electrodes 8 and 8' through a lead line inserted in the catheter tube 1.

In the catheter for temporary pacing shown in FIG. 2 the pacemaker function portion 2 is arranged at the branched portion of the catheter, and this catheter is improved in the adaptability to the catheter-inserting operation over the catheter shown in FIG. 1. A medicine injection lumen 10 and a medicine injection lumen opening 9 are arranged in the catheter for temporary pacing shown in FIG. 2. The structure and function of the pacemaker function portion 2 are the same as those of the pacemaker function portion shown in FIG. 1.

The catheter tube of the catheter for temporary pacing according to the present invention is not limited to the balloon catheter but may be a semi-floating catheter, a stylet-equipped catheter or the like.

In another embodiment of the catheter for temporary pacing according to the present invention, another temporary pacemaker is connected to the temporary pacemaker shown in FIG. 1 or 2, and this additionally attached pacemaker may be used according to need. In this embodiment, even if a problem occurs in the integrally equipped temporary pacemaker, said additionally attached pacemaker can be used instead.

The manipulating method and function of the catheter for temporary pacing according to the present invention will now described.

For a usual temporary pacing, the catheter of the present invention is manipulated in the following manner. Namely, if the catheter for temporary pacing is normally placed in contact with the heart of patient, the energy required for the stimulation is relatively small. The relationship between the pulse width and pulse amplitude necessary for stimulating the living body tissue can be approximated by a rectangular hyperbola known as Weiss formula. If a large stimulation threshold value is necessary, it is feared that the contact position of the electrode of the catheter for temporary pacing is not proper or a certain contact is not maintained. This insufficient pacing is improved by adjusting the position of the distal end of the catheter for temporary pacing. In pacing the heart, where the pulse width of the stimulation output duration is adjusted to about 2 m-sec, the distal end of the catheter for temporary pacing is held at the position at which it is confirmed that the stimulation pulse amplitude threshold value making pacing possible is smaller than 1 V. It is well known that the pulse amplitude of the above-mentioned threshold value rises with the lapse of time, and the pulse amplitude is generally set at a level at least two times the threshold value of each patient; that is, at a level higher than 2 V. In other words, even though the pulse width and pulse amplitude are fixed at values exceeding certain levels, if the distal end of the catheter for temporary pacing is located at an appropriate position in an emergency, pacing be properly performed and a short-period maintenance of patient's life is possible.

Figure 3:
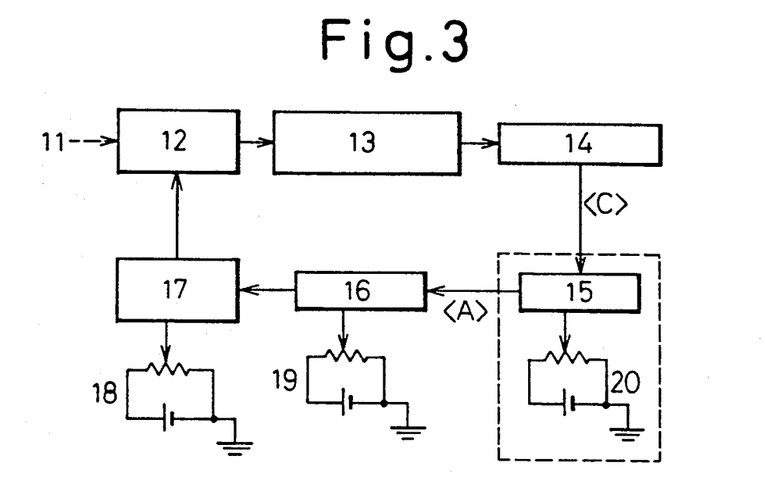
FIG. 3 is a block diagram illustrating a conventional temporary pacemaker.

FIG. 3 is a block diagram illustrating the mechanism of the conventional demand-type pacemaker (this mechanism will be described hereinafter). In the catheter for temporary pacing according to the present invention, based on the above-mentioned knowledge, it is possible to fix the pulse width and the pulse amplitude to 3 m-sec and 2.5 V, respectively, and therefore, a first variable resistor 18 can be removed from a pulse-generating circuit 17 in the conventional demand-type pacemaker shown in FIG. 3 by fixing the stimulation output amplitude.

In accordance with the circuit of the temporary conventional demand-type pacemaker shown in FIG. 3, the demand pacemaker inspects the endocardial potential of the natural heart through the temporary pacing catheter 11. The endocardial potential obtained from the temporary pacing catheter 11 through an input-output changeover circuit 12 is amplified by a preamplifier 13, and a waveform in which a noise component and a cardiac potential component other than the QRS wave are controlled is obtained through a filter 14. This processed waveform is compared with a certain but variable reference potential through a comparing circuit 15 and a third variable resistor 20.

Figure 4A:
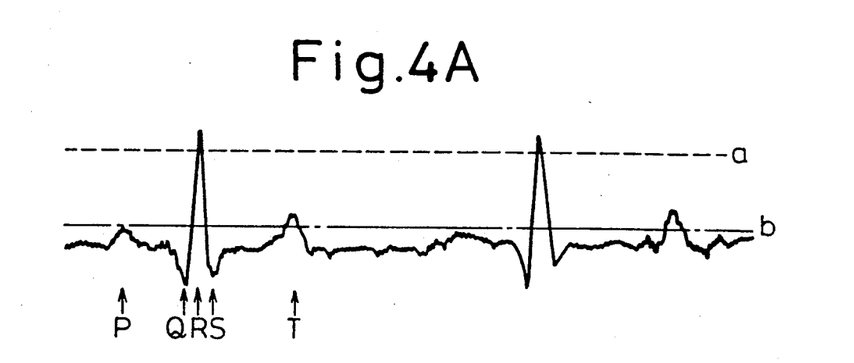
Figure 4B:
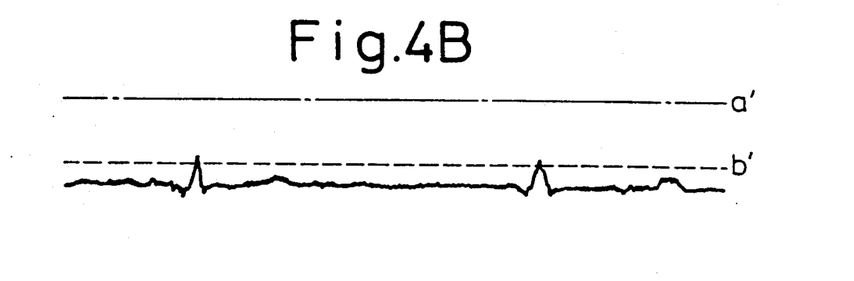

FIGS. 4A and 4B show examples of the waveform of the endocardial potential; wherein FIG. 4A shows the waveform obtained when the electrocardiographic input is large and FIG. 4B shows the waveform obtained when the electrocardiographic input is small. In FIGS. 4A and 4B, the time is plotted on the abscissa and the potential is plotted on the ordinate. Each of broken lines a and b' and one-dot broken lines b and a' indicates the reference potential.

The waveform in which the noise component and the electrocardiographic component other than the QRS wave are controlled is compared with a certain but variable reference potential, and if the condition that this controlled waveform is larger than the reference potential, the QRS wave is detected. Whether the controlled waveform is larger or smaller than the reference potential depends on whether the QRS wave is caused to rise or fall by the preamplifier and filter, but one condition is realized by arranging an absolute value circuit.

If the QRS wave is detected in the endocardial potential within a certain time as the result of the comparison, an inhibiting output is generated in the comparing circuit 15 in FIG. 3 to reset a timer 16 and inhibit the stimulation output. If the QRS wave is not detected within a certain time, the timer 16 is not reset and after the lapse of the certain time, a pulse-generating circuit 17 is actuated to put out stimulation through the temporary pacing catheter and accelerate the pulsation of the heart of the patient.

The adjustment of this certain time corresponds to the adjustment of the stimulation rate. For a short-period maintenance of life of patient in an emergency, this certain time can be selected so that the stimulation rate is in the range of from 50 to 150 pulses per minute, for example, 70 or 100 pulses per minute.

In the catheter for temporary pacing according to the present invention, by using one fixed value or making selection among two or more fixed values, the second variable resistor for adjusting the stimulation rate (19 in FIG. 3) can be removed and the size can be further reduced. A switch can be used for making selection among two or more fixed values. Thus, the temporary pacemaker portion 2 and the catheter portion 1 can be used in the integrated state as shown in FIG. 1.

The above-mentioned variable and constant reference potential is set relatively to the endocardial potential obtained from the patient through the catheter for temporary pacing so that stable pacing is possible, and this setting corresponds to the adjustment of the electrocardio-input sensitivity. In each of the case of FIG. 4A in which the electrocardio-input is large and the case of FIG. 4B where the electrocardio-input is small, the setting should be such that the reference potential a or b' intersects only the pulse of the amplified and filtered waveform represented by the broken line.

In connection with the QRS wave on the endocardial potential, especially the R wave generally having a large wave height, Furman et al. made detailed investigation (V. Decaprio, M. Hurzeler and S. Furman: A Comparison of Unipolar and Bipolar Electrograms for Cardiac Pacemaker Sensing, CIRCULATION 56, 750, 1977), and it has been clarified, where pacing can be normally carried out, the electrocardio-input sensitivity is 2 to 20 mV. If the adjustment of the electrocardio-input sensitivity is not appropriately performed, the inhibiting function does no act properly and pacing pulses are output irregularly to the natural heart, sometimes resulting in fibrillation of the ventricle.

Where the electrocardio-input sensitivity is not properly set will now be described with reference to FIGS. 4A and 4B. In FIG. 4A (the electrocardio-input is large), the reference potential b represented by the one-dot broken line corresponds to the case where the electrocardio-input sensitivity is too high, that is, the set reference potential is too low. In this case, the endocardial potential component other than the QRS wave, for example, the P wave or T wave, causes unnecessary inhibition, and stimula are not put out at an appropriate timing. In FIG. 4B (the electrocardiographic input is small), the reference potential a' represented by the one-dot broken line corresponds to the case where the electrocardio-input sensitivity is too low, that is, the set reference potential is too high. In this case, the QRS wave cannot be detected and necessary inhibition is not exerted, but unnecessary stimula are continuously put out.

In the catheter for temporary pacing according to the present invention, the comparing circuit is constructed so that the reference potential monotonously decreases to the higher sensitivity side or monotonously increases from the QRS input just preceding timewise. Whether the monotonous decrease or the monotonous increase is adopted depends on whether the QRS wave as the reference input is positive or negative.

The operation of the pacemaker of the catheter for temporary pacing according to the present invention will now be described. The following embodiments will be explained based on the presumption that the QRS wave is positive.

Figure 5:
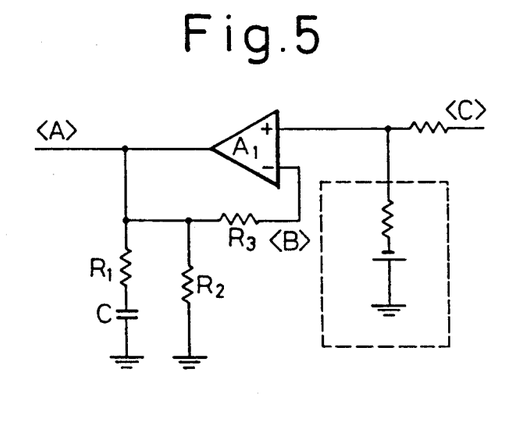
FIG. 5 is a circuit diagram illustrating an example of the mechanism of the pacemaker of the catheter for a temporary pacing according to the present invention.
Figure 6:
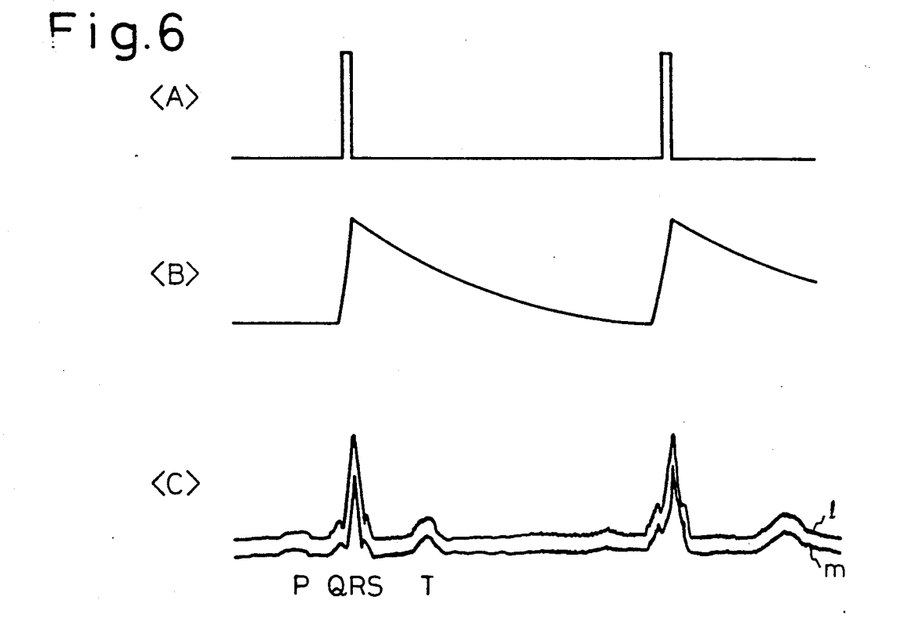
FIG. 6 shows waveforms indicating the changes with the lapse of time of the endocardial potentials at points (A), (B) and (C) in FIG. 5.

The circuit shown in FIG. 5 illustrating an embodiment of the mechanism of the pacemaker of the catheter for temporary pacing according to the present invention corresponds to the comparing circuit surrounded by the broken line in the conventional technique shown in FIG. 3. Referring to FIG. 5, if the endocardial potential is given from (C) through the filter, when the input given to (C) becomes larger than the reference potential given to (B), the output (A) of comparator A1 fully swings to the positive side. This output (A) charges C through R1 and raises up the reference potential of (B). Finally, the reference potential of (B) becomes the endocardial potential input of (C) obtained through the filter, and the output (A) of comparator A1 fully swings to a negative value or to zero. As the result, as shown in FIG. 6, in (A), a positive rectangular wave is generated at the position corresponding to the QRS wave in the endocardial electrocardiographic input of (C). From this point, the electric charge stored in C shown in FIG. 5 is discharged through R1 and R2 and the monotonous decrease is caused as shown in FIG. 6.

(A), (B) and (C) of FIG. 6 are waveforms showing the changes with the lapse of time of the endocardial potential at (A), (B) and (C) of FIG. 5, respectively. Every time the reference potential of (B) detects the QRS wave, the endocardial potential is raised up and then, this potential monotonously decreases. More specifically, at the point of detection of the QRS wave, the electrocardio-input sensitivity is set at the value that can be detected only by a QRS wave having a wave peak value equal to that of the detected QRS wave, and the electrocardio-input sensitivity is gradually changed to the higher sensitivity side with the lapse of time from this point. By this change of the electrocardio-input sensitivity with the lapse of time, the operation of comparator A1 by the P wave or T wave left through the filter can be prevented. Simultaneously, the QRS wave caused by the subsequent heartbeat can be detected assuredly. In more detail, since the reference voltage of (B) at the point when each peak value appears is sufficiently higher than the peak value of the P wave or T wave left through the filter, comparator A1 is not actuated by the P wave or T wave.

Furthermore, since the peak value of the reference potential of (B) shown in FIG. 6 is perpetually set by the QRS wave just preceding, the QRS wave can be stably detected over the broad range (2 to 20 mV) of the endocardial input.

Furthermore, by adding an offset surrounded by the broken line in FIG. 5 to the potential at point (C), an offset indicated by line m can be added to (C) in FIG. 6. By addition of this offset, if the electrocardio-input sensitivity is too high, inhibition of the pulse-generating circuit by a noise can be prevented. If the portion surrounded by the broken line in FIG. 3 is replaced by the circuit shown in FIG. 5 in the above-mentioned manner, the operation of adjusting the electrocardio-input sensitivity according to each patient by an operator in the conventional technique becomes unnecessary, and therefore, the third variable resistor for this adjustment (20 in FIG. 3) can be removed.

Figure 7:
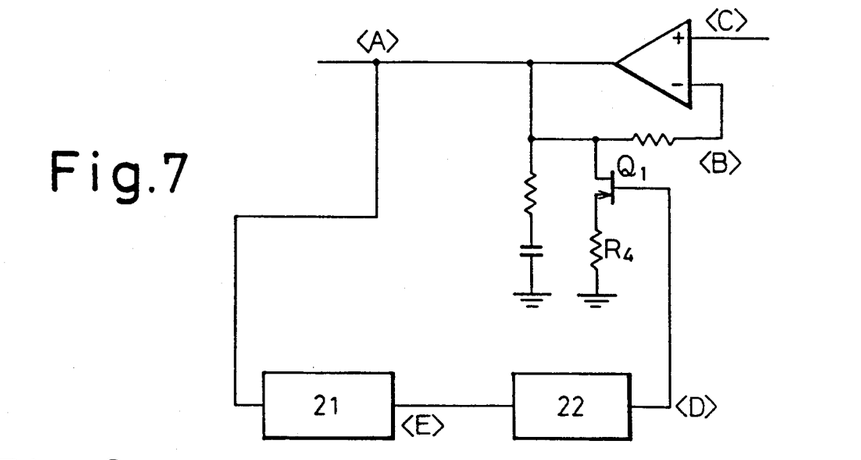
FIG. 7 is a circuit diagram showing another example of the mechanism of the pacemaker of the catheter for temporary pacing according to the present invention.
Figure 8:
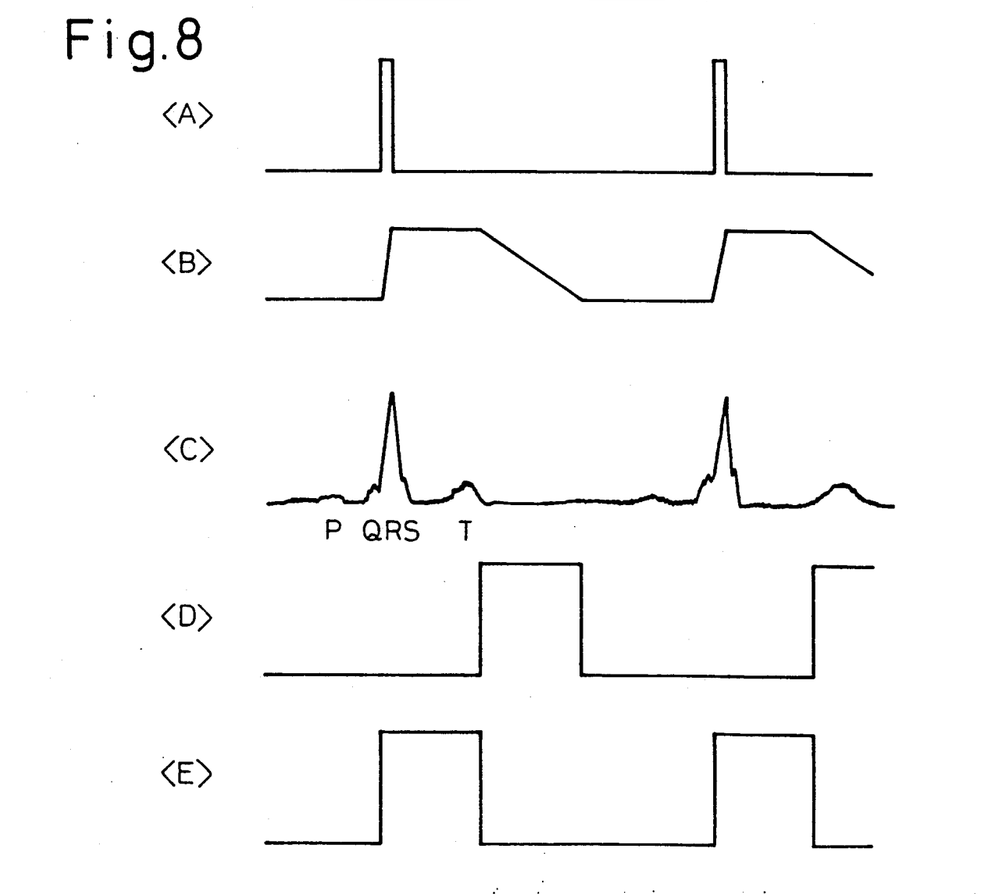
FIG. 8 shows waveforms indicating the changes with the lapse of time of endocardial potentials at points (A), (B), (C), (D) and (E) in FIG. 7.

It is important how the reference potential of (B) is changed with the lapse of time relative to the electrocardiographic input. This point will now be described with reference to FIG. 7 showing a second embodiment of the mechanism of the pacemaker of the catheter for temporary pacing according to the present invention and FIG. 8 showing the change of the endocardial potential with the lapse of time in this embodiment. Referring to FIG. 7, by replacing R2 shown in FIG. 5 by a first one-shot timer 21, a second one shot timer 22, R4 and Q1, the start of the monotonous decrease of the reference potential of (B) can be freely changed.

The first one-shot timer 21 is started by the output of detection of the QRS wave of (A). The waveform at this point is shown in (E) of FIG. 8. After the lapse of a certain time from the point just after detection of the QRS wave, (E) falls down. During this period, the reference potential shown in (B) of FIG. 8 does not substantially decrease and is different in this point from (B) of FIG. 6. In short, the reference potential shown in (B) of FIG. 8 is kept substantially constant. Then, the second one-shot timer 22 is started by the fall of (E). The output of the second one-shot timer 22 at this point is shown in (D) of FIG. 8. While the output of (D) is being generated, Q1 shown in FIG. 7 is kept in the "ON" state, and discharge of C is effected through Q1 and R4. Accordingly, as shown in (B) of FIG. 8, the potential of (B), which has been kept constant, monotonously decreases while the output is present at (D). When (D) falls, the decrease of (B) is stopped, and detection of the subsequent QRS wave is prepared for.

In the embodiment shown in FIG. 7, the operation of comparator A1 is safer than in the embodiment shown in FIG. 5, because the reference potential of (B) is higher than the T wave having a higher peak. Furthermore, in the embodiment shown in FIG. 7, although the number of constituent parts increases, the size is much smaller than that of the variable resistor for the manual adjustment, shown in FIG. 3. Namely, the total area of the two one-shot timers is several mm square and the thickness is about 1 mm, and the two one-shot timers are highly integrated.

By combining the method for discharging C, shown in FIGS. 5 and 6, with the method shown in FIGS. 7 and 8, the change of the potential at point (B) with the lapse of time can be further changed. Furthermore, the circuit is not limited to the above-mentioned two kinds or the combination thereof. For example, if the peak value of the endocardial input to (C) is detected and retained by using the output (A) at the time of detection of the QRS wave and this retained peak value is used as the starting reference potential for detection of the QRS wave and is changed to the higher sensitivity side with the lapse of time, the automatic adjustment of the input sensitivity for detection of the QRS wave can be performed practically sufficiently.

These functions can be realized by an A/D converter, a microprocessor and a software, or by other digital and analog circuits.

By incorporation of the above-mentioned function of automatically adjusting the electrocardiographic input sensitivity, the third variable resistor 20 shown in FIG. 3 can be omitted, as pointed out hereinbefore. By fixing the above-mentioned stimulation output amplitude and stimulation rate and using the circuits shown in FIGS. 5 and 7, all of the first, second and third variable resistors 18, 19 and 20 can be omitted. Accordingly, the size of the temporary pacemaker can be greatly diminished and the temporary pacemaker can be integrally built in the catheter for temporary pacing, as shown in FIGS. 1 and 2.

The catheter for temporary pacing according to the present invention, in which the small-size temporary pacemaker is built, can be packaged in the sterilized condition with a packaging material, and the catheter for temporary pacing according to the present invention can be stored in this packaged state and be handed to an operator at the time of the treatment.

Furthermore, in accordance with the present invention, there is provided a pacing catheter comprising a balloon attached to the distal end of the catheter, said balloon being arranged so that when the balloon is inflated, the balloon envelops an electrode at the distal end of the catheter.

Figure 9:
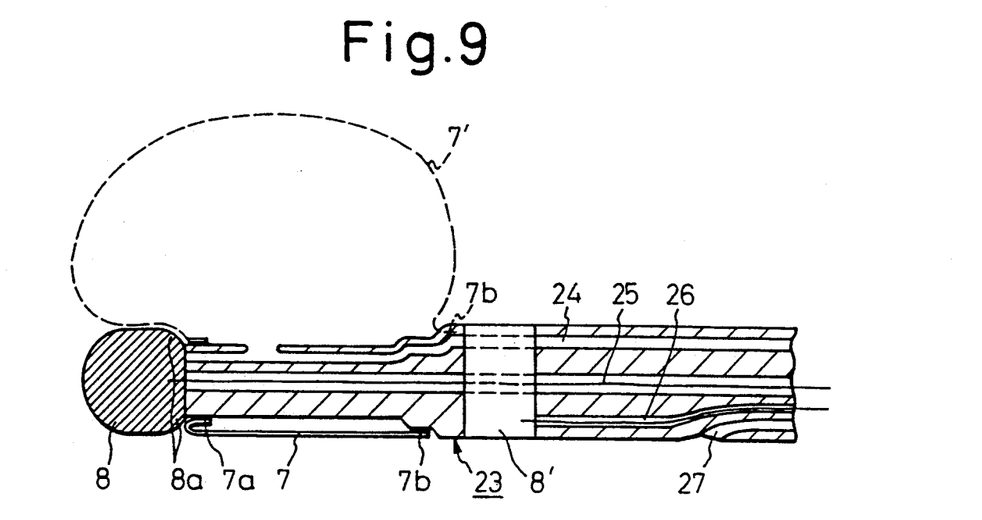
FIG. 9 is a sectional view showing the vicinity of the distal end in one embodiment of the pacing catheter of the present invention.
Figure 10:
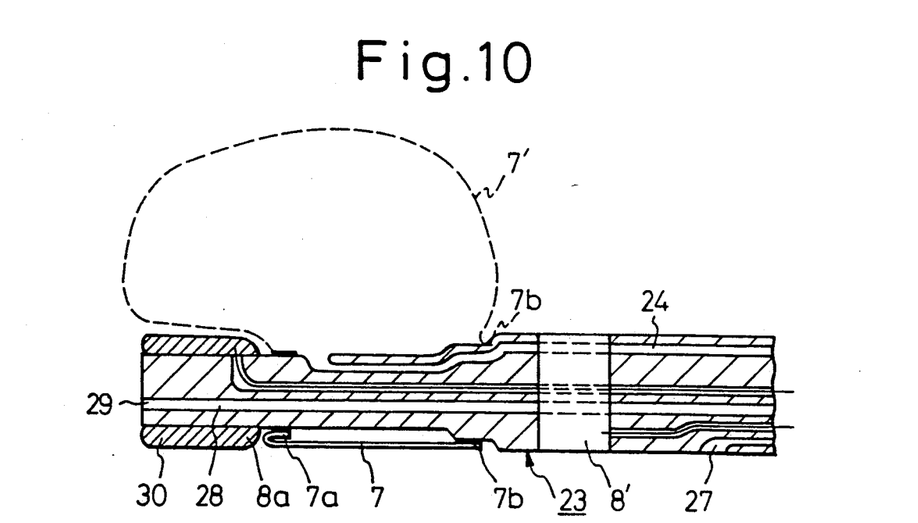
FIG. 10 is a sectional view showing the vicinity of the distal end of another embodiment of the pacing catheter according to the present invention.

This balloon pacing catheter will now be described with reference to FIGS. 9 and 10. In FIGS. 9 and 10, a balloon 7 (7') is attached to the vicinity of the distal end of a catheter 23, and the balloon is inflated by feeding air through a balloon lumen 24, and the balloon is deflated by releasing air from the lumen 24. For convenience, both the inflated balloon 7' and the deflated balloon 7 are shown in FIGS. 9 and 10. A pacing electrode 8 is attached to the distal end of the catheter 23, and a second pacing electrode 8' can be further arranged according to need. Furthermore, if necessary, a medicine injection opening 27 is formed in the vicinity of the distal end of the catheter 23, preferably on the side face at a point 10 to 15 cm apart from the electrode 8 at the distal end. The body portion of the catheter 23 is preferably composed of an antithrombogenic material, and silicone, polyurethane and the like are preferred. The balloon 7 (7') is preferably composed of an elastic material excellent in the pressure sensitivity, the mechanical properties and the antithrombogenic property, and silicone rubber, polyurethane, natural rubber and the like can be used. To maintain a shape enveloping the top end electrode when the balloon 7 is inflated, preferably the distal end portion 7a of the balloon is attached to the catheter 23 in the lapelled condition, while the manner of attaching the other end 7b of the balloon is not particularly critical. The balloon 7 attached to the catheter portion 1 is inflated by feeding air from the balloon lumen 24 to form an inflated shape 7' enveloping the electrode 8 at the distal end.

The electrodes 8 and 8' are usually composed of stainless steel, platinum or the like and are connected to the exterior of the catheter through lead lines inserted through electrode lumina 25 and 26 preferably the electrode 8' in the vicinity of the distal end is arranged with a distance of 1.0 to 2.0 cm from the top end electrode. Since the electrode 8 at the distal end is enveloped by the inflated balloon 7'. The electrode 8 is designed so that the length in the longitudinal direction is sufficiently short. The portion 8a, to be placed in contact with the balloon 7', of the electrode 8 at the distal end is appropriately rounded so that the balloon is not damaged by the contact when the balloon is inflated.

FIG. 10 shows a modification of the balloon pacing catheter shown in FIG. 9. This modification is advantageous over the balloon pacing catheter shown in FIG. 9 in the following points. More specifically, an annular electrode 30 at the distal end is equivalent to the above-mentioned electrode 8 at the distal end in the capacity of transmitting the stimulating electric current to the intended part from the pacemaker efficiently, but since the distal end pressure of the catheter can be measured, the insertion to the intended part can be performed precisely. Namely, since the annular electrode 30 at the distal end covers the distal end portion of the catheter and a measurement lumen 28 for measuring the distal end pressure of the catheter is opened as a distal end hole 29 of the catheter, a pressure-measuring device is connected to the distal end (not shown) side of the catheter fluid-communicating with the distal end hole, and insertion and holding can be accomplished while measuring the distal end pressure of the catheter. More specifically, this modification is advantageous in that by measuring the distal end pressure of the catheter, an operator of the catheter can easily grasp the position of the distal end of the catheter in the blood vessel or heart even without using a fluoscopic equipment.

In each of the foregoing embodiments, the pacing catheter having bipolar electrodes is illustrated, but a pacing catheter having a monopolar electrode or tripolar or higher polarity electrodes can be used.

INDUSTRIAL APPLICABILITY

Since the catheter for temporary pacing according to the present invention has a very small temporary pacemaker which can be fixed to an appropriate position of the body of a patient, the transfer of the patient can be performed very conveniently. Moreover, the manufacturing cost is low.

Furthermore, if the pacing catheter is packaged in the sterilized condition, problems or another's help required for the connection of the pacemaker to the catheter and various adjustments in the conventional technique can be avoided, and therefore, the pacing catheter of the present invention is suitable for an emergency treatment.

Moreover, since a balloon taking a shape enveloping and covering the distal end electrode when inflated is attached, the risk of the damage to the heart or blood vessel at the time of insertion of the catheter can be eliminated, and the catheter can be caused to flow in the heart and blood vessel safely and promptly.

Still further, by attaching a distal end electrode having an annular structure, the distal end pressure can be measured while retaining the above-mentioned balloon shapes, and therefore, the distal end electrode can be held at the intended part precisely. Moreover, since this distal end electrode is brought into contact with the intended part within the heart, the simulating current from the pacemaker connected to the proximal end of the catheter can be efficiently transmitted to this intended part.

We claim:

1. A temporary pacing catheter, comprising:
   an integrally attached pacemaker having a stimulation frequency and a stimulation output; and
   adjusting means for automatically adjusting an electrocardio-input sensitivity, said adjusting means including;
   a) a comparator having an output and a first and second input,
   b) first and second parallel resistances coupled to said output,
   c) a third resistance coupled to said second parallel resistance,
   d) wherein said first input of said comparator is an endocardial potential, and said second input to said comparator is connected to said third resistance, forming a feedback loop from said output, said feedback loop being connected to a grounding conductor through said first and second parallel resistances, said first resistance being connected in series with a capacitor;

wherein one or both of the stimulation frequency and the stimulation output are fixed.

2. A temporary pacing catheter according to claim 1, wherein said second resistance is connected in series with a transistor having a drain, a source and a gate; said drain is connected in parallel with said first resistance and said comparator output, said source is connected to said second resistance, and said gate is connected to at least one one-shot timer.

3. A temporary pacing catheter according to claim 2, wherein one of said one-shot timers is connected to said comparator output.

* * * * *